US011213499B1

(12) United States Patent
Kunwar et al.

(10) Patent No.: US 11,213,499 B1
(45) Date of Patent: Jan. 4, 2022

(54) USE OF 3,3'-DISELENODIPROPIONIC ACID (DSEPA) AS AN ANTICANCER AGENT

(71) Applicant: Secretary, Department of Atomic Energy, Mumbai (IN)

(72) Inventors: Amit Kunwar, Mumbai (IN); Vishwa Vipulkumar Gandhi, Mumbai (IN); Khushboo Atulkumar Gandhi, Mumbai (IN); Vikram Suryaprakash Gota, Mumbai (IN); Jayant Sastri Goda, Mumbai (IN); Jyoti Anand Kode, Mumbai (IN); Liladhar Baburao Kumbhare, Mumbai (IN); Vimal Kumar Jain, Mumbai (IN); Kavirayani Indira Priyadarsini, Mumbai (IN)

(73) Assignee: Secretary, Department of Atomic Energy, Mumbai (IN)

( * ) Notice: Subject to any disclaimer, the term of this patent is extended or adjusted under 35 U.S.C. 154(b) by 0 days.

(21) Appl. No.: 17/003,420

(22) Filed: Aug. 26, 2020

(51) Int. Cl.
*A61K 31/194* (2006.01)
*A61P 35/00* (2006.01)

(52) U.S. Cl.
CPC ............ *A61K 31/194* (2013.01); *A61P 35/00* (2018.01)

(58) Field of Classification Search
None
See application file for complete search history.

(56) References Cited

U.S. PATENT DOCUMENTS 2,556,451 A 6/1951 Smith
2,729,676 A 1/1956 MacPeek

FOREIGN PATENT DOCUMENTS

KR 101690179 B1 12/2016
WO 2016204561 A1 12/2016

OTHER PUBLICATIONS

Cao et al., Oncotarget (2014), 5(17), pp. 7431-7445.*
Carroll et al., "Interaction kinetics of selenium-containing compounds with oxidants", Free Radical Biology and Medicine, 2020, pp. 58-68, vol. 155.
Gandhi et al., "Oral administration of 3,3-diselenodipropionic acid prevents thoracic radiation induced pneumonitis in mice by suppressing NF-KB/IL-17/G-GSF/neutrophil axis", Free Radical Biology and Medicine, 2019, vol. 145, pp. 3-19.
Gao et al., "A Spherical Nucleic Acid Probe Based on Au—Se Bond", Analytical Chemistry, 2020, pp. 8459-8463, vol. 92, No. 12.
Gota et al., "Biodistribution and Pharmacokinetic Study of 3,3' Diseleno Dipropionic Acid (DSePA), A Synthetic Radioprotector, in Mice", European Journal of Drug Metabolism and Pharmacokinetics, 2015, pp. 839-844, vol. 41, No. 6.
Kunwar et al., "3,3'-Disenelodipropionic Acid, an Efficient Peroxyl Radical Scavenger and a GPx Mimic, Protects Erythrocytes (RBCs) from AAPH-lnduced Hemolysis", Chemical Research in Toxicology, 2007, pp. 1482-1487, vol. 20, No. 10.
Kunwar et al., "In vivo radioprotection studies of 3,3'-diselenodipropionic acid, a selenocysine derivative", Free Radical Biology & Medicine, 2010, pp. 399-410, vol. 48, No. 3.
Kunwar et al., "Anti-apoptotic, anti-inflammatory, and immunomodulatory activities of 3,3'-diselenodipropionic acid in mice exposed to whole body y-radiation". Archives of Toxicology, 2011, pp. 1395-1405, vol. 85, No. 11.
Kunwar et al., "A Selenocysteine Derivative Therapy Affects Radiation-Induced Pneumonitis in the Mouse", American Journal of Respiratory Cell and Molecular Biology, 2013, pp. 654-661, vol. 49, No. 4.
Kunwar et al., "Toxicological safety evaluation of 3,3'-diselenodipropionic acid (DSePA), a pharmacologically mportant derivative of selenocystine", Regulatory Toxicology and Pharmacology, 2018, pp. 159-167, vol. 99.
Singh et al., "In silico investigation on the binding of organoselenium compounds with target proteins of SARS-CoV-2 nfection cycle", ChemRxiv, 2020, 31 pages, retrieved from https://doi.org/10.26434/chemrxiv.12594134.v1.

* cited by examiner

Primary Examiner — Brian J Davis
(74) Attorney, Agent, or Firm — The Webb Law Firm

(57) ABSTRACT

The present invention describes the method of using a synthetic organoselenium compound, DSePA for management of non-small cell lung carcinoma (NSCLC) and chronic myelogenous leukemia (CML). The method comprises administering DSePA orally at a dosage of 1 mg/Kg body weight daily for inhibiting the growth of A549 (representative of NSCLC) and K562 (representative of CML) tumor in mice models. Additionally, the said compound also inhibits the proliferation of other cancer cells of NSCLC (HOP-62 and H460), breast (MDA-MB-231), white blood cells (JURKAT and U-937), oral (SCC-40), colon (HT-29), kidney (A498) and cervix (SiHA) origins in cellular models at a much lower concentration than that needed to inhibit the growth of normal cells.

14 Claims, 5 Drawing Sheets

Figure 3:
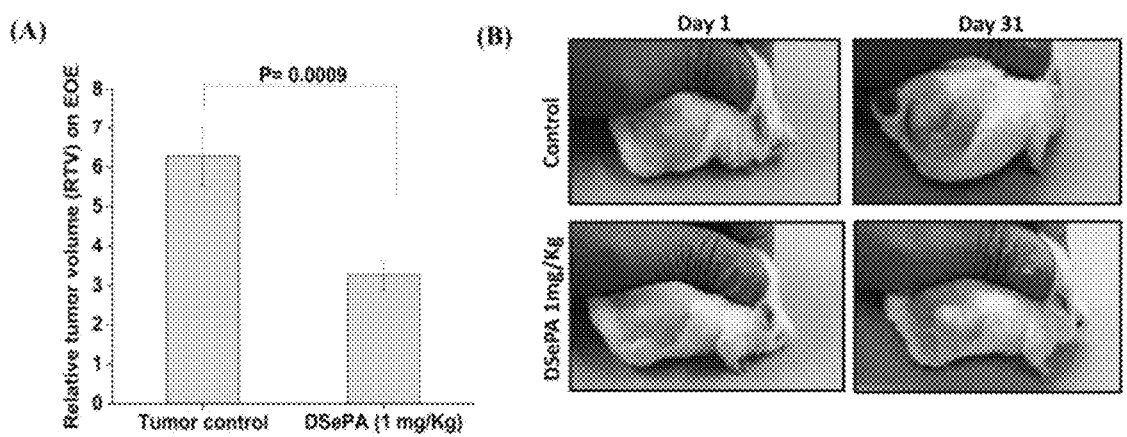

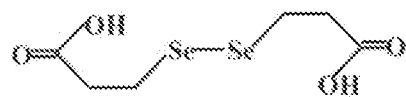
Fig. 1 - Prior Art
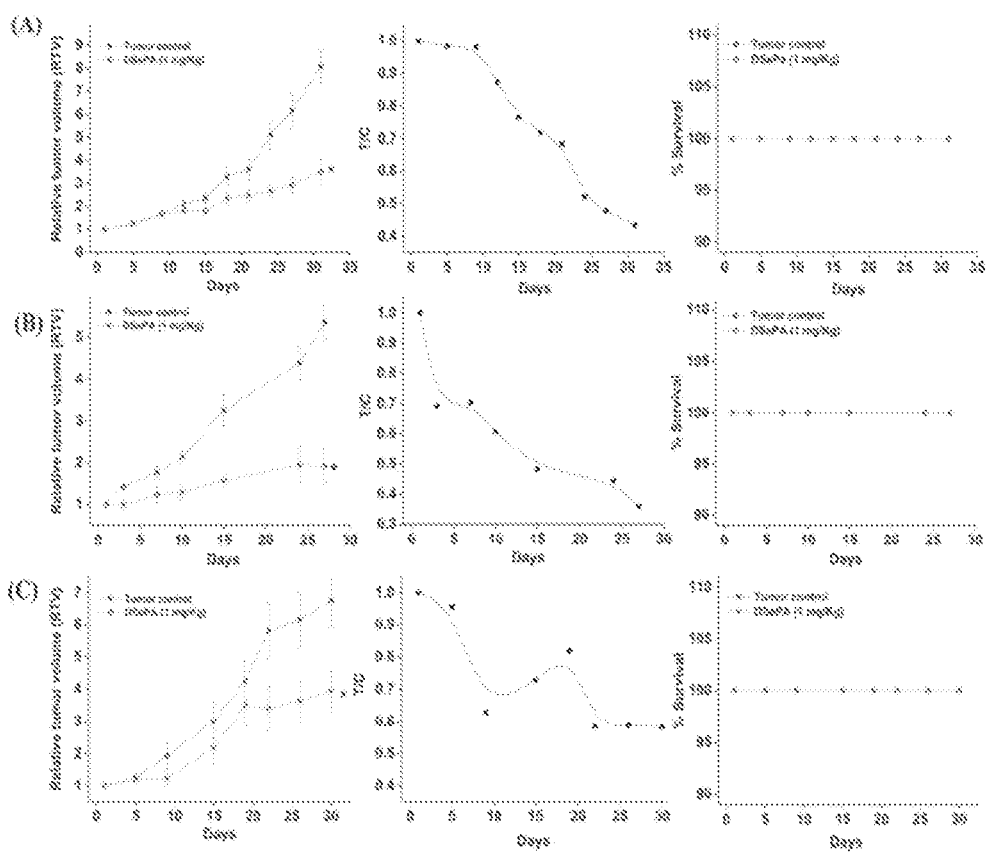
Fig. 2

USE OF 3,3'-DISELENODIPROPIONIC ACID (DSEPA) AS AN ANTICANCER AGENT

FIELD OF INVENTION

The present invention relates to the field of medicine and pharmaceuticals. In specific, the invention describes the method of using a synthetic organoselenium compound, DSePA for management of non small cell lung carcinoma (NSCLC) and chronic myelogenous leukemia (CML). The method comprises administering DSePA orally at a dosage of 1 mg/Kg body weight daily for inhibiting the growth of A549 (representative of NSCLC) and K562 (representative of CML) tumor in mice models. Additionally, the said compound also inhibits the proliferation of other cancer cells of NSCLC (HOP-62 and H460), breast (MDA-MB-231), white blood cells (JURKAT and U-937), oral (SCC-40), colon (HT-29), kidney (A498) and cervix (SiHA) origins in cellular models at a much lower concentration than that needed to inhibit the growth of normal cells.

BACKGROUND OF THE INVENTION

Cancer is a major public health problem worldwide. The global cancer burden is estimated to have risen to 18 million new cases and 9.6 million deaths in 2018. Lung cancer is the most common cancer in terms of incidence, and is ranked within the top five in terms of mortality. Further, Leukemia is one of the most common childhood cancers, but it most often occurs in older adults. Management of lung cancers requires multimodal approach of surgery, chemotherapy, radiation therapy and targeted therapy either alone or in combination. Chemotherapy along with radiotherapy forms a major backbone in the adjuvant therapy for any cancer. However, optimizing cancer therapy still poses a challenge to the treating oncologist due to unwanted and often morbid side effects of these agents. Moreover, complete eradication of malignant tumor clones is often not achieved due to therapeutic resistance to the available treatment regimes. In this context, NSCLC and CML have a very aggressive natural course and develop resistance to conventional chemotherapeutic agents rather early during treatment. Further, majority of chemotherapeutic drugs used for the treatment of cancers are administered through intravenous route. However oral administration has a far greater appeal in terms of clinical utility as this route is non-invasive and may increase the patient compliance. Hence it is imperative to develop newer compounds which are not only effective anticancer agents against NSCLC and CML but are also patient compliant.

Lately, selenium a micronutrient in different chemical forms for humans and animals has gained a lot of attention as a pharmacological agent. Organoselenium compounds can protect normal cells from oxidative damage as they get incorporated into antioxidant selenoproteins like glutathione peroxidase (GPx) and thioredoxin reductase (TrxR). On the other hand, they can be toxic to tumour cells by inducing oxidative stress and apoptosis. This differential activity of the compound depends on its chemical structure, bioavailability and the cellular redox state. In this context, a number of selenium compounds such as sodium selenite, selenocystine, selenomethionine, methyl selenocysteine and methylseleninic acid have been evaluated for anticancer effects either alone or in combination with other anticancer drugs, however none of these could be translated till date to the clinic.

On similar lines, DSePA, a water-soluble derivative of selenocystine has previously been reported for antioxidant, radioprotective, nitric oxide (NO) generating and neuroprotective activities in cells and mice model systems. Notably DSePA is also shown to be orally bio-available with maximum uptake in lung compared to other organs. However, there are no reports on the method of using DSePA per se as an anticancer agent. The inventors hypothesized that DSePA might be effective in killing human cancer cells through oral route of administration. In order to address the above said hypothesis, the inventors evaluated the anticancer activity of DSePA in human cancer cell lines of different tissue and pathological origins.

Prior Patents Relating to 3,3'-Diselenodipropionic Acid (DSePA)

U.S. Pat. No. 2,556,451A relates to a fungicidal insulating composition. This invention relates to a hot melt coating material that is moisture and fungus resistant and more particularly to a coating material capable of successfully withstanding both the extremely low and extremely high temperatures that might be encountered in transportation and use of electrical equipment, and which is highly effective in preventing fungicidal development or attack on its surfaces. This patent deals with fungicidal property of DSePA.

U.S. Pat. Nos. 2,729,676A and 352,053A teach about preparation of beta, beta'-diselenodipropionic acid. This invention relates to fungicidal compounds and more particularly to new compositions of matter having pronounced fungicidal activity. This patent deals with fungicidal property of DSePA but no disclosure of anticancer activity.

KR101690179B1 relates to a method for manufacturing radiation responsive chitosan nanoparticles in which radioprotective amifostine is covalently bonded and crosslinked by DSePA. The radiation responsive chitosan nanoparticle combined with amifostine can protect the human body from exposure to radiation and it can minimize side effect on the human body by releasing the amifostine, when human body is exposed by the radiation. This patent deals with chitosan conjugated amifostine and DSePA for its radioprotection effect and not of anticancer activity WO2016204561A1 relates to a method for preparing a radioresponsive nanoparticle using DSePA as a linker to which a radioprotector is bound. The radioprotector-combined nanoparticle according to the invention has the features of being capable of preventing adverse effects on the human body by preventing the release of a radioprotector in the absence of radiation exposure, and protecting tissues and cells from radiation exposure by effectively releasing a radioprotector in the presence of radiation exposure. This patent deals with chemical utility of DSePA but no disclosure of anticancer activity.

Journal of Free Radical Biology and Medicine 145 (2019) 8-19 by Gandhi et al relates to a publication titled "Oral administration of 3,3-diselenodipropionic acid prevents thoracic radiation induced pneumonitis in mice by suppressing NF-KB/IL-17/G-GSF/neutrophil axis". It discloses the use of DSePA (2.5 mg/kg body weight orally three times a week) in preventing and delaying the incidence of symptomatic radiation induced lung pneumonitis (RILP), a major dose limiting side effect of thoracic radiotherapy.

Similarly, Journal of Free Radical Biology and Medicine 148(2010) 399-410 & American Journal of Respiratory Cell Molecular Biology 49 (2013) 654-661 by Amit Kunwar, et al relate to publications titled "In vivo radioprotection studies of 3,3-diselenodipropionic acid a selenocystine derivative" and "A selenocysteine derivative therapy delays and reduces radiation-induced neutrophilia and pneumonitis in the mouse" respectively. These publications disclose the radio-protective activity of DSePA (2 mg/kg body weight intraperitoneally three times a week) against whole body or thoracic exposure to gamma radiation.

Further, Journal of Regulatory Toxicology and Pharmacology 99(2018) 159-167 by Amit Kunwar et al relates to a publication titled "Toxicological safety evaluation of 3,3-diselenodipropionic acid (DSePA), a pharmacologically important derivative of selenocystine". It discloses that DSePA, a pharmacologically important derivative of selenocystine has been evaluated for acute toxicity, mutagenic safety and metabolic stability. The estimated median oral Lethal dose ($LD_{50}$) cut-off of DSePA in mice and rat model are 200 mg/kg and 25 mg/kg respectively, which is considerably higher than the reported oral dose of its parent compound, selenocystine.

OBJECTS OF THE INVENTION

An object of the present invention is to propose the use of DSePA (chemical structure shown in FIG. 1) as an effective anti-cancer agent for the treatment of human NSCLC and CML.

Another object of the present invention is to evaluate the anticancer activity of DSePA in human cancer cell lines of different tissue and pathological origins using cellular models.

Still further object of the present invention is to propose a potential broad-spectrum anticancer agent.

Yet another object of the present invention is to propose an efficacious, water soluble and easily administrable anticancer agent.

BRIEF DESCRIPTION OF THE INVENTION

According to this invention, there is provided the use of synthetic organoselenium compound (DSePA) as an effective anticancer agent for the treatment of NSCLC (A549) and CML (K562).

In accordance to this invention, there is also provided a method of treatment of cancer comprising; administering the said DSePA orally at a dosage of 1 mg/kg body weight daily for four weeks for inhibiting the growth of NSCLC (A549) and CML (K562).

Additionally, the said compound also inhibits the proliferation of other cancer cells of NSCLC (HOP-62 and H460), breast (MDA-MB-231), white blood cells (JURKAT and U-937), oral (SCC-40), colon (HT-29), kidney (A498) and cervix (SiHA) origins under in vitro conditions with growth inhibitory (GI50) concentration of ≤10 μM.

BRIEF DESCRIPTION OF THE ACCOMPANYING DRAWINGS

Figure 4:
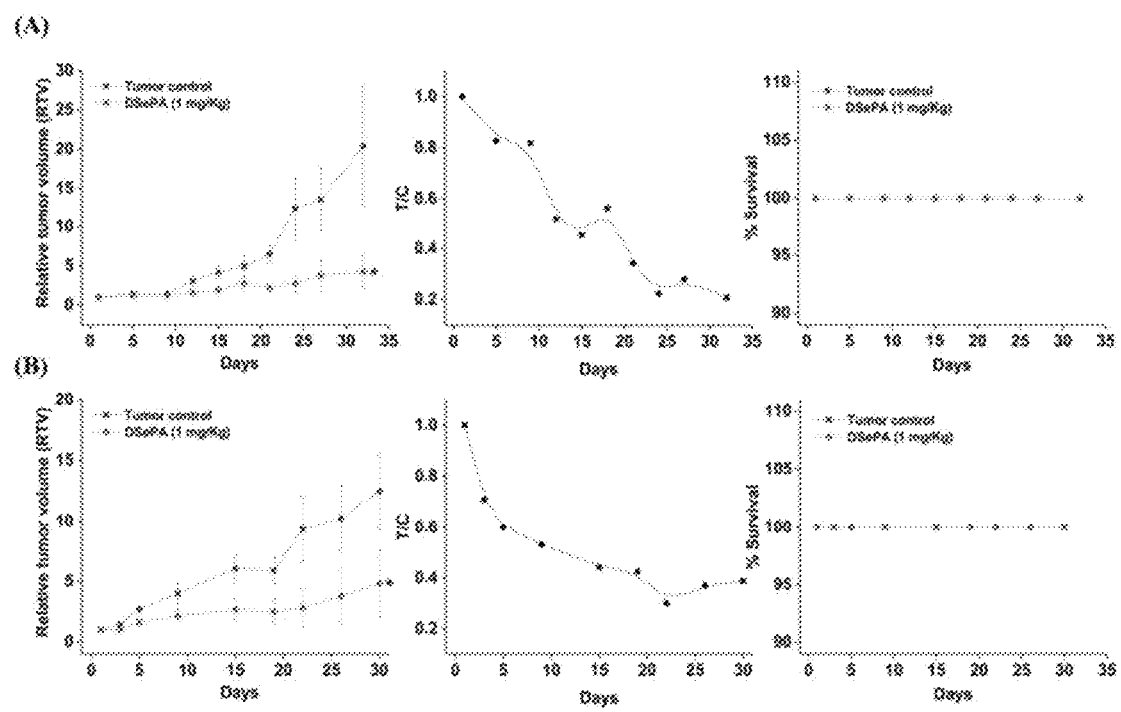
Figure 5:
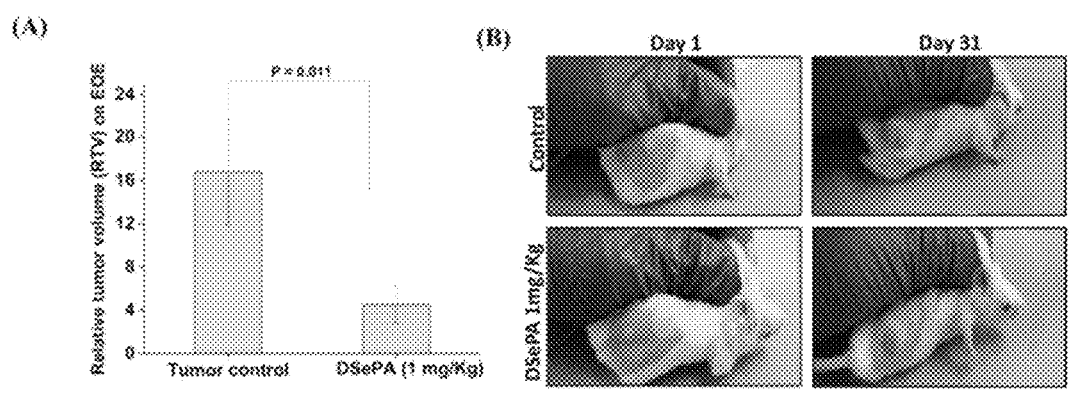
Figure 6:
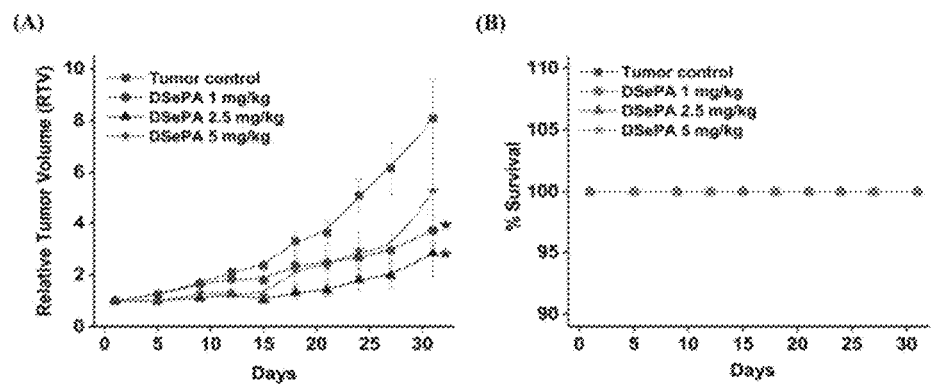
Figure 7:
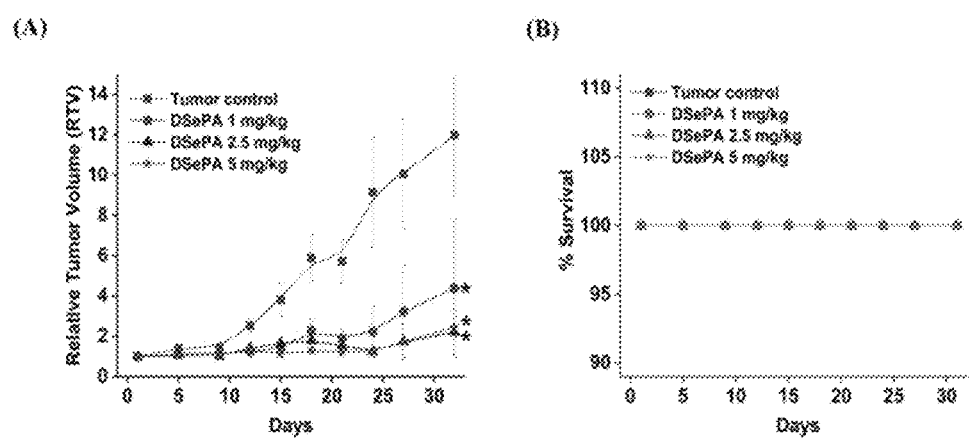

FIG. 1. Chemical structure of DSePA.
FIG. 2. The anti-tumor effect of DSePA (1 mg/kg orally daily) in human A549 xenograft model: (A), (B) & (C) show changes in the relative tumor volume (RTV) (left panel), T(test)/C(control) value (middle panel) and percent (%) survival (right panel) of different treatment groups as a function of time in days obtained from three independent studies respectively. The results are presented as mean±SEM (n=6). *<0.05 as compared to tumor control group by T Test.
FIG. 3. (A) Bar graph shows the mean fold changes in the relative tumor volume (RTV) of DSePA (1 mg/kg orally daily) treated group as compared to tumor control group on the end of experiment (EOE) or day 30 in human A549 xenograft model. The results are presented as mean±SEM (n=18). *<0.05 as compared to tumor control group by T Test. (B) Representative images show the effect of DSePA treatment on the extent of tumor growth in human A549 xenograft model.
FIG. 4. The anti-tumor effect of DSePA (1 mg/kg orally daily) in human K562 xenograft model: (A) & (B) show changes in the relative tumor volume (RTV) (left panel), T(test)/C(control) value (middle panel) and percent (%) survival (right panel) of different treatment groups as a function of time in days obtained from two independent studies respectively. The results are presented as mean±SEM (n=6). *<0.05 as compared to tumor control group by T Test.
FIG. 5. (A) Bar graph shows the mean fold changes in the relative tumor volume (RTV) of DSePA (1 mg/kg body orally daily) treated group as compared to tumor control group on the end of experiment (EOE) or day 30 in human K562 xenograft model. The results are presented as mean±SEM (n=12). *<0.05 as compared to tumor control group by T Test. (B) Representative images show the effect of DSePA treatment on the extent of tumor growth in human K562 xenograft model.
FIG. 6. (A) Changes in relative tumor volume (RTV) show the anti-tumor effect of the different treatment doses (1, 2.5 and 5 mg/kg orally daily) of DSePA in human A549 xenograft model. The results are presented as mean±SEM (n=6). *<0.05 as compared to tumor control group by T Test. (B) Mice survival data is plotted as a function of post-treatment time (30 days).
FIG. 7. (A) Changes in relative tumor volume (RTV) show the anti-tumor effect of the different treatment doses (1, 2.5 and 5 mg/kg orally daily) of DSePA in human K562 xenograft model. The results are presented as mean±SEM (n=6). *<0.05 as compared to tumor control group by T Test. (B) Mice survival data is plotted as a function of post-treatment time (30 days).

DETAILED DESCRIPTION OF THE INVENTION

The anticancer effect of DSePA was evaluated using a panel of twenty-five human cancer cell lines of different tissue origins. Cells were treated with the increasing concentrations (0.1-100 μM) of DSePA for 48 h and viability was monitored by (Sulforhodamine B) SRB assay or MTT assay. The results indicated that DSePA treatment inhibited the growth/proliferation of human cancer cell types such as leukemia (Jurkat and U-937), breast cancer (MDA-MB-231) and cervix cancer (SiHa) with $GI_{50}$ (half maximal concentration to inhibit proliferation/growth by 50%) value of ≤1 μM and of lung cancer (A549, HOP-62 and H460), kidney cancer (A-498), oral cancer (SSC-40) and colon cancer (HT-29) with $GI_{50}$ of ≤10 μM (Table—1). Notably DSePA treatment in the similar concentration range did not show toxicity in normal cell types such as WI-38 (human normal lung fibroblast), Vero (monkey kidney cell lines) and CHO (Chinese Hamster Ovarian epithelial cell line) (Table-1).

Based on these results, in vivo studies were undertaken to evaluate the anticancer effects of DSePA on A549 & K562 xenografts in mice. These xenografts representative of NSCLC and CML respectively are considered to be highly aggressive and resistant to chemotherapy treatment. Therefore, any new chemotherapy agent against these cancers is very much sought. For the experiment, a total of 12 mice bearing A549 or K562 tumors of volume in the range of ~50 mm$^3$ were divided into two groups (I & II), each group comprising of six mice. The group I did not receive any treatment and served as tumor control group. The group II was administered DSePA daily dissolved in sterile saline through oral route at a dosage of 1 mg/Kg body weight. The tumor volume and body weight of mice from each group were monitored daily for a total period of 30 days from the day of start. The animals were also checked for mortality if any throughout the study period. The experiment in A549 tumor was repeated three times (n=18 for each group) and the experiment in K562 tumor was repeated two times (n=12 for each group). The results indicated that administration of DSePA at the dosage of 1 mg/Kg body weight significantly (P<0.05) inhibited the growth of A549 and K562 tumors in mice as evidenced by the successive decrease in their T/C values in each of the independent experiments (FIG. 2 & FIG. 4). In line with this observation, DSePA treatment showed an overall reduction of ~2 folds (P=0.0009) and ~3.7 folds (P=0.011) in A549 and K562 models by the end of study period (30 days) (FIG. 3 & FIG. 5). It is also worth to mention that mice from DSePA treated groups (1 mg/Kg) did not show any mortality during the study period of 30 days (FIG. 2 & FIG. 4). This is the first study to show the anticancer activity of DSePA per se using xenograft model of human lung cancer (A549) and human leukemia (K562) cells in mice. Discovery of the application of the anticancer activity of DSePA is a novel invention in context of its probable usage in treatment for lung and leukemia cancer. More specifically the invention proposes a treatment regime and route of administering DSePA to inhibit the growth of human NSCLC (A549) and CML (K562).

The major limitations in the clinical translation of selenium compounds for anticancer application have been the mode of administration and inherent toxicity. DSePA, a structural derivative of selenocystine has following listed advantages over other selenium compounds for anticancer effects:

1) The present invention provides the method and dosage of DSePA to be administered to achieve a significant therapeutic efficacy against certain cancer types like NSCLC and CML. Notably the said compound was found to be effective through oral (daily) route of administration. As per National Cancer Institute (NCI) guide line, a compound can be considered for anticancer application only if it exhibits T/C (mean tumor volume of drug treated group)/(mean tumor volume of control)≤0.42. Our study has indicated that DSePA achieved T/C≤0.42 in lung & leukemia models under the invented treatment dosage (1 mg/kg body weight daily). This suggests its potential as an anticancer agent.

2) Since chemotherapeutic drugs presently used in clinics are mostly delivered through intravenous route, DSePA showing anticancer activity through oral route gains a lot of significance in terms patient compliance. The efficacious dosage of DSePA was 1 mg/kg body weight and the further increase in dosage did not show any significant increase in the efficacy in NSCLC and CML models. The previous publications have established that DSePA is considerably lesser toxic than its parent compound selenocystine and other chemical forms of selenium commonly used as nutritional supplement such as sodium selenite, methylselenocysteine and selenomethionine. Taken together, DSePA is a less toxic and effective derivative of selenocystine for management of cancer. However, its dosage and treatment schedule may vary in human depending on cancer types and in combination to radiation therapy.

Data on Dosage Optimization

For the optimization of the oral dosage of DSePA, a total of 24 mice bearing A549 or K562 xenograft of volume in the range of ~50 mm$^3$ were divided into four groups (I-IV), each group comprising of six mice. The group I did not receive any treatment and served as tumor control group. The groups II, III and IV were administered DSePA dissolved in sterile saline through oral route at the dosage of 1, 2.5 and 5 mg/kg body weight respectively. The administration of DSePA was performed daily for 4 weeks. The tumor volume and body weight of mice from each group were monitored daily for a total period of 30 days from the day of start. The animals were also checked for mortality if any throughout the study period. The results indicated that administration of DSePA at the doses of 1 and 2.5 mg/kg body weight significantly (P<0.05) inhibited the growth of A549 tumor from day 21 onwards till the experimental end point (31' day) (Table—2 & FIG. 6). Notably groups treated with 1 and 2.5 mg/kg body weight of DSePA did not show any significant difference in tumor volume at the experimental end point (31$^{st}$ day) (Table—2 & FIG. 6). A higher dosage of 5 mg/kg of DSePA did not show any significant suppression of A549 tumor at the experimental end point (31$^{st}$ day) as compared to control group (Table—2 & FIG. 6). On the other hand, administration of DSePA at all the three dosage of 1, 2.5 and 5 mg/kg body weight significantly (P<0.05) inhibited the growth of K562 tumor from the day 15 onwards (Table-3 & FIG. 7). The statistical analysis did not show any significant difference between 1, 2.5 and 5 mg/kg treatment groups (Table—3 & FIG. 7). This clearly suggested that the minimum dosage of DSePA to achieve optimum efficacy against both A549 and K562 tumor models is 1 mg/kg body weight (Table—2, Table—3, FIG. 6 & FIG. 7). It is also worth to mention that mice from DSePA treated groups (1, 2.5 and 5 mg/kg) did not show any mortality during the study period of 30 days in both tumor models (Table—2, Table—3, FIG. 6 & FIG. 7).

TABLE 1

Anti-proliferative activity of DSePA in human cancer cell lines as studied by SRB/MTT assay. The cells were treated with 0.1 μM, 1.0 μM, 10.0 μM and 100 μM of DSePA for 48 hours prior to SRB and/or MTT assay. The experiments were done in triplicates.

| Cell lines | Cancer type (tissue) | GI$_{50}$ (μM) |
| --- | --- | --- |
| JURKAT | Human T cell leukemia | <0.1** |
| U-937 | Human myelomonocytic leukemia | 0.03** |
| MDA-MB-231 | Human breast cancer (triple negative) | <0.1** |
| A549 | Human non-small cell lung adenocarcinoma | 10* |
| HOP-62 | Human non-small cell lung adenocarcinoma | 1* |
| H460 | Human non-small cell lung adenocarcinoma | 8* |
| A-498 | Human kidney cancer | 2* |
| SiHa | Human cervical cancer | <0.1* |
| SCC-40 | Human oral squamous cell carcinoma | 2* |
| HT-29 | Human colon cancer | 1* |
| WI-38 | Human normal lung fibroblast | >100 |
| Vero | Monkey kidney transformed epithelial cell line (normal) | >100 |
| CHO | Chinese Hamster Ovary (normal) | >100 |

GI$_{50}$ = Concentration of drug causing 50% inhibition of cell growth
** = Significant anti-proliferative activity
* = Moderate anti-proliferative activity

TABLE 2

Table shows the anti-tumor effect of the different treatment doses of DSePA in human A549 xenograft model. The results are presented as mean ± SEM (n = 6).

| Days (Treatment) | Untreated | | | 1 mg/kg body weight daily oral | | | 2.5 mg/kg body weight daily oral | | | 5 mg/kg body weight daily oral | | |
|---|---|---|---|---|---|---|---|---|---|---|---|---|
| | RTV | T/C | % S | RTV | T/C | % S | RTV | T/C | % S | RTV | T/C | % S |
| 1 | 1 | — | 100 | 1 | 1 | 100 | 1 | 1 | 100 | 1 | 1 | 100 |
| 5 | 1.24 ± 0.07 | — | 100 | 1.23 ± 0.06 | 0.98 | 100 | 0.99 ± 0.05 | 0.79 | 100 | 0.94 ± 0.04 | 0.75 | 100 |
| 9 | 1.67 ± 0.18 | — | 100 | 1.64 ± 0.08 | 0.98 | 100 | 1.10 ± 0.12 | 0.66 | 100 | 1.29 ± 0.10 | 0.76 | 100 |
| 12 | 2.09 ± 0.17 | — | 100 | 1.83 ± 0.13 | 0.87 | 100 | 1.25 ± 0.12 | 0.59 | 100 | 1.30 ± 0.14 | 0.62 | 100 |
| 15 | 2.35 ± 0.19 | — | 100 | 1.80 ± 0.17 | 0.76 | 100 | 1.03 ± 0.13 | 0.43 | 100 | 1.19 ± 0.16 | 0.50 | 100 |
| 18 | 3.30 ± 0.37 | — | 100 | 2.36 ± 0.25 | 0.71 | 100 | 1.31 ± 0.25 | 0.39 | 100 | 2.22 ± 0.56 | 0.67 | 100 |
| 21 | 3.61 ± 0.45 | — | 100 | 2.47 ± 0.27 | 0.68 | 100 | 1.40 ± 0.22 | 0.38 | 100 | 2.34 ± 0.59 | 0.65 | 100 |
| 24 | 5.11 ± 0.61 | — | 100 | 2.66 ± 0.30 | 0.52 | 100 | 1.81 ± 0.39 | 0.35 | 100 | 2.94 ± 0.72 | 0.57 | 100 |
| 27 | 6.15 ± 0.99 | — | 100 | 2.94 ± 0.36 | 0.47 | 100 | 1.96 ± 0.48 | 0.31 | 100 | 2.92 ± 0.64 | 0.47 | 100 |
| 31 | 8.08 ± 1.52 | — | 100 | 3.70 ± 0.54*,# | 0.45 | 100 | 2.84 ± 0.91*,# | 0.35 | 100 | 5.30 ± 2.06 | 0.65 | 100 |

RTV = Relative Tumor Volume;
T/C = T (test)/C (control);
S = Survival
*<0.05 - Treatment groups of 1 mg/kg and 2.5 mg/kg are significantly different as compared to tumor control group by T Test.
Treatment groups of 1 mg/kg and 2.5 mg/kg are significantly not different for parameters like RTV and T/C by T Test

TABLE 3

Table shows the anti-tumor effect of the different treatment doses of DSePA in human K562 xenograft model. The results are presented as mean ± SEM (n = 6).

| Days (Treatment) | Untreated | | | 1 mg/kg body weight daily oral | | | 2.5 mg/kg body weight daily oral | | | 5 mg/kg body weight daily oral | | |
|---|---|---|---|---|---|---|---|---|---|---|---|---|
| | RTV | T/C | % S | RTV | T/C | % S | RTV | T/C | % S | RTV | T/C | % S |
| 1 | 1 | — | 100 | 1 | 1 | 100 | 1 | 1 | 100 | 1 | 1 | 100 |
| 5 | 1.42 ± 0.07 | — | 100 | 1.13 ± 0.05 | 0.80 | 100 | 1.09 ± 0.13 | 0.76 | 100 | 1.04 ± 0.06 | 0.73 | 100 |
| 9 | 1.43 ± 0.08 | — | 100 | 1.13 ± 0.05 | 0.79 | 100 | 1.01 ± 0.06 | 0.70 | 100 | 1.05 ± 0.06 | 0.73 | 100 |
| 12 | 2.52 ± 0.34 | — | 100 | 1.22 ± 0.12 | 0.48 | 100 | 1.42 ± 0.26 | 0.56 | 100 | 1.32 ± 0.20 | 0.52 | 100 |
| 15 | 3.82 ± 0.81 | — | 100 | 1.42 ± 0.18 | 0.37 | 100 | 1.66 ± 0.23 | 0.43 | 100 | 1.11 ± 0.09 | 0.29 | 100 |
| 18 | 5.88 ± 1.16 | — | 100 | 2.28 ± 0.56 | 0.38 | 100 | 1.79 ± 0.32 | 0.30 | 100 | 1.29 ± 0.15 | 0.22 | 100 |
| 21 | 5.72 ± 1.08 | — | 100 | 1.90 ± 0.42 | 0.33 | 100 | 1.54 ± 0.29 | 0.26 | 100 | 1.22 ± 0.15 | 0.21 | 100 |
| 24 | 9.14 ± 2.71 | — | 100 | 2.22 ± 1.25 | 0.24 | 100 | 1.23 ± 0.24 | 0.13 | 100 | 1.25 ± 0.12 | 0.13 | 100 |
| 27 | 10.06 ± 2.71 | — | 100 | 3.24 ± 2.30 | 0.32 | 100 | 1.74 ± 0.89 | 0.17 | 100 | 1.73 ± 0.37 | 0.17 | 100 |
| 32 | 11.98 ± 3.00 | — | 100 | 4.38 ± 3.44*,# | 0.36 | 100 | 2.21 ± 1.09*,# | 0.18 | 100 | 2.45 ± 0.48*,# | 0.20 | 100 |

RTV = Relative Tumor Volume;
T/C = T (test)/C (control);
S = Survival
*<0.05 - Treatment groups of 1 mg/kg and 2.5 mg/kg are significantly different as compared to tumor control group by T Test.
Treatment groups of 1 mg/kg and 2.5 mg/kg and 5 mg/kg are significantly not different for parameters like RTV and T/C by T Test.

EXAMPLES

Cell culture and DSePA synthesis—DSePA was synthesized and characterized as described in our previous reports. Cell lines were cultured in growth medium (DMEM/RPMI) supplemented with 10% FBS, 100 U/ml penicillin and 100 µg/ml streptomycin at 37° C. in a humidified 5% $CO_2$ environment. The stock solution of DSePA was prepared fresh in cell culture medium and diluted with the same to achieve the desired concentrations.

SRB/MTT Assay—To evaluate the anti-proliferative effect of DSePA, Cells (~5×10$^3$) suspended in 100 µl of complete culture medium were seeded in each well of 96 well plates. The cells were allowed to attach and grow for 24 h, treated with desired concentrations of DSePA dissolved in culture medium for 48 h and then processed for SRB/MTT assay as described in literature. The percentage (%) cytotoxicity was calculated from the decrease in absorbance as compared to that of control group.

Animal maintenance—All animal studies were approved by the Institutional Animal Ethics Committee. Animals were housed under standard conditions (20±2° C., 65-70% humidity, 12 h/12 h day/night cycle, balanced laboratory diet and tap water ad libitum.

Xenograft tumor model-A549 and K562 tumor models were developed by Anticancer Drug Screening Facility of Advanced Centre for Treatment, Research and Education in Cancer (ACTREC), India. Briefly, Male/female NOD-SCID aged 6-7 weeks were housed in the laboratory animal facility of ACTREC. Donor mice carrying K562 or A549 xenografts were developed by injecting 2×10$^6$ cells in 100 µl of DMEM/RPMI, subcutaneously in their right flank. When tumors attained the size of approximately 2000 mm$^3$, the animals were sacrificed. Tumors were obtained and further cut into 2-3 mm fragments and implanted subcutaneously in the right flank of 6-7 weeks old recipient SCID mice. Tumors were allowed to grow to a size of approximately 50 mm$^3$ following which animals were divided into groups of six animals each for evaluation. A fresh DSePA solution was prepared by dissolution in sterile saline before each administration by intraperitoneal/oral route. The tumor efficacy of DSePA was determined by monitoring parameters like tumor volume and T/C. Tumors were assumed spherical and volume was calculated using following equations (1 & 2):

$$\text{Tumor volume }(cc) = \left[\frac{4\pi}{3}((d_{av})/2)^3\right]/1000 \quad (1)$$

$$d_{av} = \frac{(d_1 + d_2)}{2} \quad (2)$$

Where d1 (mm) and d2 (mm) are diameters measured in two perpendicular planes. T/C is defined as the ratio of the mean tumor volume of DSePA treated groups with the mean tumor volume of control group on the day of observation.

We claim:

1. A method of inhibiting the growth of Non-Small Cell Lung Cancer and Chronic Myeloid Leukemia, the method comprising administering 3,3'-diselenodipropionic acid (DSePA) orally at a dose in the range of 1 mg/kg to 5 mg/kg body weight.

2. The method of claim 1, wherein the DSePA is administered daily for four weeks.

3. The method of claim 1, wherein the DSePA is administered at a dose in the range of 1.0 mg/kg to 1.9 mg/kg body weight.

4. The method of claim 1, wherein the DSePA is administered at a dosage of 2.6 mg/kg to 4.9 mg/kg body weight.

5. A method of inhibiting the growth/proliferation of human cells of leukemia, lung cancer, renal cancer, oral cancer, colon cancer, and cervix cancer comprising treating/incubating said cells with 3,3'-diselenodipropionic acid (DSePA) in vitro.

6. The method of claim 5, wherein the cells are treated with DSePA at a concentration of 0.1 µM to 10 µM.

7. The method of claim 5, wherein the DSePA is administered in a concentration that does not inhibit growth of non-cancerous cells.

8. The method of claim 1, wherein the non-small cell lung cancer is an A549 cell type and the chronic myeloid leukemia is a k562 cell type.

9. The method of claim 5, wherein the leukemia is a JURKAT or U-937 cell type.

10. The method of claim 5, wherein the lung cancer is a HOP-62 or H460 cell type.

11. The method of claim 5, wherein the renal cancer is an A498 cell type.

12. The method of claim 5, wherein the oral cancer is an SSC-40 cell type.

13. The method of claim 5, wherein the colon cancer is an HT-29 cell type.

14. The method of claim 5, wherein the cervix cancer is an SiHa cell type.

* * * * *